United States Patent
Sung

(10) Patent No.: US 11,052,038 B2
(45) Date of Patent: Jul. 6, 2021

(54) FACIAL CLEANSING TISSUE WITH NATURAL PLANT ORIGIN AND PREPARATION METHOD THEREOF

(71) Applicant: TENART BIOTECH LIMITED, Taipei (TW)

(72) Inventor: Mei-Shih Sung, Taipei (TW)

(73) Assignee: TENART BIOTECH LIMITED, Taipei (TW)

(*) Notice: Subject to any disclaimer, the term of this patent is extended or adjusted under 35 U.S.C. 154(b) by 101 days.

(21) Appl. No.: 16/172,923

(22) Filed: Oct. 29, 2018

(65) Prior Publication Data

US 2020/0129416 A1 Apr. 30, 2020

(51) Int. Cl.
*A61K 8/97* (2017.01)
*A61Q 1/14* (2006.01)
*A61Q 19/10* (2006.01)
*A61K 8/02* (2006.01)

(52) U.S. Cl.
CPC .............. *A61K 8/97* (2013.01); *A61K 8/0208* (2013.01); *A61Q 1/14* (2013.01); *A61Q 19/10* (2013.01)

(58) Field of Classification Search
None
See application file for complete search history.

(56) References Cited

U.S. PATENT DOCUMENTS

2012/0048769 A1* 3/2012 Sivik ....................... B29C 43/22
206/524.1

\* cited by examiner

*Primary Examiner* — Isis A Ghali

(57) ABSTRACT

Disclosed are a green environmental facial cleansing tissue with a natural plant origin and its preparation method, particularly a green facial cleansing tissue with a makeup removal function and a natural plant origin formula and its preparation method. The formula of the facial cleansing tissue consists of natural plants, honey extracts, etc., and the facial cleansing tissue is capable of avoiding skin irritation, providing a convenient and safe use, and the facial cleansing tissue is naturally decomposable and environmentally friendly.

2 Claims, No Drawings

FACIAL CLEANSING TISSUE WITH NATURAL PLANT ORIGIN AND PREPARATION METHOD THEREOF

FIELD OF INVENTION

The present invention relates to a green environmental facial cleansing tissue product with a natural plant formula, in particular to a green facial cleansing tissue with a natural plant origin and a makeup removal function, and a preparation method of the green facial cleansing tissue, and such facial cleansing tissue is naturally decomposable and environmentally friendly.

BACKGROUND OF INVENTION

1. Description of the Related Art

With the improvement of people's living standards, cosmetics especially facial products become increasingly more popular in our daily life, and facial cleansing products become the products with the first priority to people in pursuit of facial skincare.

Secondly, since makeup products are very popular, base makeup products are often applied to a relatively large area of a user's face, so that the makeup removal has become a prelude to skincare. The makeup removal related products generally include cleansing oils, facial cleansing lotions, facial cleansers, etc.

However, it is still necessary to use a facial cleanser after removing the makeups, and the sequence and process are relatively complicated, and some of the consumers particularly the young female and male consumers are overwhelmed by the sequence of use. Therefore, we need to develop an innovative facial cleansing product with a makeup removal function in order to overcome the aforementioned issues all at a time.

With the pursuit of environmental protection and green natural life and materials, a foam ingredient of a low-stimulation green plant origin is the first choice for safe skincare.

In addition, most regular cleansing and makeup removing products have high water content. However, when a traveler carries liquid cosmetics with them to a flight, the volume of liquid cosmetics is limited and kept under 100 ml for the aviation safety consideration. Therefore, more and more cosmetics are developed with an easy-to-carry, concentrated, and light form.

It is noteworthy that the green facial cleansing tissue with a natural plant origin and the makeup removal function becomes a primary development goal in the makeup removal and facial cleansing market.

In view of the aforementioned drawbacks of the prior art, the inventor of the present invention based on years of experience in the related industry to conduct extensive research and experiments, and finally developed a facial cleansing tissue with a natural plant formula and invented a preparation method of such facial cleansing tissue to simplify the steps of facial cleansing and skincare significantly. In addition, the main ingredients come from natural plants, honey extract, etc., and the invention is capable of avoiding skin irritation, and providing a convenient and safe use, and the facial cleansing tissue of the invention is naturally decomposable and environmentally friendly.

2. Summary of the Invention

In view of the deficiencies of the prior art and the market requirements, it is a primary object of the present invention to provide a facial cleansing tissue using a natural plant origin (tapioca starch) as a forming agent, amino acids and alkyl glycosides extracted from sapindaceae and green environmental foaming agent, and various plant extracts to achieve a multifunctional face cleansing, makeup removal and skincare effect, and the facial cleansing tissue is naturally decomposable and environmentally friendly.

To achieve the aforementioned and other objectives, the present invention provides a facial cleansing tissue with a natural plant origin, wherein the facial cleansing tissue is made of a slurry after being dehydrated, and the slurry contains a starch with a formula of the slurry and the starch in the ratio of 4:1, and the starch is a tapioca starch or its modified starch, and the slurry is formed by mixing an ingredient A, an ingredient B, an ingredient C and an ingredient D, and the starch is a tapioca starch or its modified starch, and the slurry is formed by mixing an ingredient A, an ingredient B, an ingredient C and an ingredient D.

Wherein, the ingredient A consists of 30.000~50.000% of deionized water, 36.000~44.000% of a foaming agent, and 0.050~0.100% of a chelating agent with respect to the total weight percentage of the slurry of the facial cleansing tissue;

the ingredient B consists of 1.900~3.500% of a xanthan gum with respect to the total weight percentage of the slurry of the facial cleansing tissue;

the ingredient C consists of 1.000~5.000% of an organic oil, 10.000~15.000% of an organic extract, 0.100~0.200% of a moisturizer, and 1.000~2.000% of a honey extract and/or a silk peptide with respect to the total weight percentage of the slurry of the facial cleansing tissue; and the ingredient D consists of 0.400~1.000% of an antiseptic with respect to the total weight percentage of the slurry of the facial cleansing tissue.

In an exemplary embodiment, the foaming agent is a combination of sodium lauroyl sarcosinate (SLS) and malto~oligosaccharide (MOS) and consists of 28.000~32.000% of sodium lauroyl sarcosinate (SLS) and 8.000~12.000% of malto~oligosaccharide (MOS) with respect to the total weight percentage of the slurry of the facial cleansing tissue.

In an exemplary embodiment, the sodium lauroyl sarcosinate (SLS) is a sapindus mukorossi fruit extract with a green plant origin.

In an exemplary embodiment, the chelating agent is ethylenediaminetetraacetic acid disodium salt dihydrate (EDTA).

In an exemplary embodiment, the organic oil is shea butter, sweet almond oil, Monaco argan oil or any combination of the above.

In an exemplary embodiment, the organic extract is a green tea extract, a pomegranate seed extract, a rose hydrosol or any combination of the above.

In an embodiment, the moisturizer is sodium hyaluronate.

In an exemplary embodiment, the combination of the honey extract and/or the silk peptide consists of 0.000~1.000% of the honey extract and 1.000~2.000% of the silk peptide with respect to the total weight percentage of the slurry of the facial cleansing tissue.

In an exemplary embodiment, the antiseptic is a compound of phenoxyethanol and ethylhexyl glycerin, and consists of 0.300~0.800% of phenoxyethanol and 0.100~0.200% of ethylhexyl glycerin with respect to the total weight percentage of the slurry of the facial cleansing tissue.

The present invention further provides a preparation method of a facial cleansing tissue based on the aforementioned formula, and the preparation method comprises the following steps:

(1) Heat a first mixture of deionized water, foaming agent, and organic oil at 80~85° C. until the first mixture having a total weight percentage of the slurry is dissolved completely and then stir the mixture uniformly.

(2) Dissolve a second mixture of antiseptic, xanthan gum, moisturizer, honey extract and/or silk peptide, and organic extract at normal temperature until the second mixture having a total weight percentage of the slurry is dissolved completely and then add the second mixture into the first mixture obtained from the step (1) to produce the slurry.

(3) Add starch of a specific proportion into the slurry obtained from the step (2), and use a high-speed stirring and dispersing apparatus to stir starch into a slurry mixture.

(4) Put the slurry mixture obtained from the step (3) into a paper tube, while adjusting the temperature of reaction.

(5) Rotate the paper tube at a speed of 3~7 r/s to evaporate the moisture of the paper tube completely in order to turn the slurry obtained from the step (4) into a piece of paper gradually.

(6) Roll the paper by a roll stamping machine, and then cut the paper according to a predetermined specification, and finally stamp the paper to form the facial cleansing tissue by the stamping machine.

To make it easier for our examiner to understand the objective, technical characteristics, structure, innovative features, and performance of the invention, we use exemplary embodiments for the detailed description of the invention.

BRIEF DESCRIPTION OF THE DRAWINGS

None

DESCRIPTION OF THE PREFERRED EMBODIMENTS

Exemplary Embodiment 1

In a facial cleansing tissue with a natural plant origin and its preparation method in accordance with the first exemplary embodiment of the present invention, the facial cleansing tissue is made of a slurry after being dehydrated, and the slurry consists of starch with a formula of the slurry and starch in the ratio of 4:1. The starch is tapioca starch or its modified starch, and the slurry is formed by mixing an ingredient A, an ingredient B, an ingredient C, and an ingredient D, wherein:

The ingredient A consists of 47.650% of deionized water, 28.000% of sodium lauroyl sarcosinate (SLS), 8.000% of malto~oligosaccharide (MOS), and 0.050% of ethylenediaminetetraacetic acid disodium salt dihydrate (EDTA) with respect to the total weight percentage of the slurry of the facial cleansing tissue.

The ingredient B consists of 2.500% of xanthan gum with respect to the total weight percentage of the slurry of the facial cleansing tissue.

The ingredient C consists of 0.900% of shea butter, 0.700% sweet almond oil, 0.400% of Monaco argan oil, 10.000% of organic extract, 0.100% of sodium hyaluronate, and 1.000% of silk peptide with respect to the total weight percentage of the slurry of the facial cleansing tissue.

The ingredient D consists of 0.500% of phenoxyethanol, and 0.200% of ethylhexyl glycerin with respect to the total weight percentage of the slurry of the facial cleansing tissue.

The preparation method of this exemplary embodiment comprises the following steps:

(1) Heat a first mixture of deionized water, foaming agent, organic oil mixed according the aforementioned proportion to 80~85° C. to dissolve the mixture completely, and stir the mixture uniformly.

(2) Dissolve a second mixture of antiseptic, xanthan gum, moisturizer, honey extract and/or silk peptide, and organic extract mixed according to the aforementioned proportion at normal temperature until the second mixture is dissolved completely, and then add the second mixture into the first mixture obtained from the step (1) to produce slurry.

(3) Add starch into the slurry obtained from the step (2) according to the aforementioned proportion, and stir the starch and slurry by a high-speed stirring and dispersing apparatus to form a slurry mixture.

(4) Put the slurry mixture obtained from the step (3) into a paper tube, while adjusting the temperature of reaction.

(5) Rotate the paper tube at a speed of 5 r/s to evaporate the moisture completely to turn the slurry mixture obtained from the step (4) into a piece of paper gradually.

(6) Roll the paper by a roll stamping machine, and then cut the paper according to a predetermined specification, and finally stamp and form the facial cleansing tissue by the stamping machine.

Experiment tests show that the facial cleansing tissue (which is a face and eye/lip makeup removal product) manufactured according to the method of this embodiment has a mild cleansing effect, an easy-to-clean feature, a significant BB cream/lipstick removal effect, and a mediocre mascara/eyeliner removal effect (with slight residues).

Exemplary Embodiment 2

The ingredients of the slurry of the facial cleansing tissue of this embodiment include slurry and starch mixed with a ratio of 4:1, and the starch is tapioca starch or its modified starch, and the slurry is formed by mixing an ingredient A, an ingredient B, an ingredient C and an ingredient D, wherein:

The ingredient A consists of 43.900% of deionized water, 29.000% of sodium lauroyl sarcosinate (SLS), 9.000% of malto~oligosaccharide (MOS), and 0.100% of ethylenediaminetetraacetic acid disodium salt dihydrate (EDTA) with respect to the total weight percentage of the slurry of the facial cleansing tissue.

The ingredient B consists of 2.200% of xanthan gum with respect to the total weight percentage of the slurry of the facial cleansing tissue.

The ingredient C consists of 0.700% of shea butter, 0.500% of sweet almond oil, 0.300% of Monaco argan oil, 12.000% of organic extract, 0.100% of sodium hyaluronate, 0.500% of honey extract, and 1.000% of silk peptide with respect to the total weight percentage of the slurry of the facial cleansing tissue.

The ingredient D consists of 0.500% of phenoxyethanol, and 0.200% of ethylhexyl glycerin with respect to the total weight percentage of the slurry of the facial cleansing tissue.

The facial cleansing tissue of this embodiment is manufactured by the same procedure as described in the first exemplary embodiment. Experiment tests show that the facial cleansing tissue (which is a face and eye/lip makeup removal product) manufactured according to the method of this embodiment has a mild cleansing effect, an easy-toclean feature, a significant BB cream/lipstick removal effect, and a good mascara/eyeliner removal effect (without any residues).

Exemplary Embodiment 3

The ingredients of the slurry of the facial cleansing tissue of this embodiment include slurry and starch mixed with a ratio of 4:1, wherein the starch is tapioca starch or its modified starch, and the slurry is formed by mixing an ingredient A, an ingredient B, an ingredient C, and an ingredient D, wherein:

The ingredient A consists of 39.950% of deionized water, 31.000% of sodium lauroyl sarcosinate (SLS), 11.000% of malto~oligosaccharide (MOS), and 0.100% of ethylenediaminetetraacetic acid disodium salt dihydrate (EDTA) with respect to the total weight percentage of the slurry of the facial cleansing tissue.

The ingredient B consists of 2.200% of xanthan gum with respect to the total weight percentage of the slurry of the facial cleansing tissue.

The ingredient C consists of 0.700% of shea butter, 0.500% of sweet almond oil, 0.300% of Monaco argan oil, 12.000% of organic extract, 0.050% sodium hyaluronate, 0.500% of honey extract, and 1.000% of silk peptide with respect to the total weight percentage of the slurry of the facial cleansing tissue.

The ingredient D consists of 0.500% of phenoxyethanol, and 0.200% of ethylhexyl glycerin with respect to the total weight percentage of the slurry of the facial cleansing tissue.

The facial cleansing tissue of this embodiment is manufactured by the same procedure as described in the first exemplary embodiment. Experiment tests show that the facial cleansing tissue (which is a face and eye/lip makeup removal product) manufactured according to the method of this embodiment has a mild cleansing effect with much foam and a relatively low cleansing effect, but a significant BB cream/lipstick removal effect, and a good mascara/eyeliner removal effect (with slight foam residues).

What is claimed is:

1. A preparation method for a facial cleansing tissue, wherein the facial cleansing tissue is made from a dehydrated base product, the base product containing a slurry and a starch with a formula of the slurry and the starch in a ratio of 4:1, the starch being a tapioca starch or a modified starch thereof, and the slurry being formed by mixing an ingredient A, an ingredient B, an ingredient C, and an ingredient D, wherein:
   the ingredient A consists of:
      30.000~50.000% of deionized water,
      36.000~44.000% of a foaming agent consisting of one or more of sodium lauroyl sarcosinate (SLS) and malto~oligosaccharide (MOS), and
      0.050~0.100% of ethylenediaminetetraacetic acid disodium salt dihydrate (EDTA) as a chelating agent,
   each with respect to the total weight percentage of the slurry of the facial cleansing tissue;
   the ingredient B consists of 1.900~3.500% of a xanthan gum with respect to the total weight percentage of the slurry of the facial cleansing tissue;
   the ingredient C consists of:
      1.000~5.000% of an organic oil selected from the group consisting of shea butter, sweet almond oil, and Monaco argan oil, or a combination thereof,
      10.000~15.000% of an organic extract selected from the groups consisting of a green tea extract, a pomegranate seed extract, and a rose hydrosol, or a combination thereof,
      0.100~0.200% of sodium hyaluronate as a moisturizer, and
      1.000~2.000% of a honey extract or a silk peptide, or both,
   each with respect to the total weight percentage of the slurry of the facial cleansing tissue; and
   the ingredient D consists of 0.400~1.000% of an antiseptic with respect to the total weight percentage of the slurry of the facial cleansing tissue, the antiseptic consisting of one or more of phenoxyethanol and ethylhexyl glycerin;
   wherein the preparation method comprises steps of:
   (1) heating a first mixture of the deionized water, the foaming agent, and the organic oil at 80~85□ until the first mixture is dissolved completely, and then stirring the mixture;
   (2) dissolving a second mixture of the antiseptic, the xanthan gum, the moisturizer, the honey extract or the silk peptide, and the organic extract at room temperature until the second mixture is dissolved completely, and then adding the second mixture into the first mixture obtained from step (1) to produce the slurry;
   (3) adding the starch into the slurry obtained from step (2), and using a stirring and dispersing apparatus to form the base product;
   (4) putting tile base product obtained from step (3) into a paper tube;
   (5) rotating the paper tube at a speed of 3 to 7 revolutions per second to remove moisture from the paper tube completely to turn the base product obtained from the step (4) into a paper product; and
   (6) rolling the paper product using a roll stamping machine, cutting the paper product, and stamping the paper product to form the facial cleansing tissue.

2. The preparation method for a facial cleansing tissue according to claim 1, wherein the foaming agent is a combination of sodium lauroyl sarcosinate (SLS) and malto~oligosaccharide (MOS) and consists of 28.000~32.000% of sodium lauroyl sarcosinate (SLS) and 8.000~12.000% of malto~oligosaccharide (MOS) with respect to the total weight percentage of the slurry of the facial cleansing tissue;
   wherein the sodium lauroyl sarcosinate (SLS) is a sapindus mukorossi fruit extract;
   wherein the combination of the honey extract and the silk peptide consists of 0.000~1.000% of the honey extract and 1.000~2.000% of the silk peptide with respect to the total weight percentage of the slurry of the facial cleansing tissue; and
   wherein the antiseptic is a compound of phenoxyethanol and ethylhexyl glycerin, and consists of 0.300~0.800% of phenoxyethanol and 0.100~0.200% of ethylhexyl glycerin with respect to the total weight percentage of the slurry of the facial cleansing tissue.

* * * * *